United States Patent [19]

Miyazaki et al.

[11] 4,410,722

[45] Oct. 18, 1983

[54] PROCESS FOR PREPARING OXALIC ACID DIESTERS USING PLATINUM GROUP METALS SUPPORTED ON ALUMINA

[75] Inventors: Haruhiko Miyazaki; Yasushi Shiomi, both of Ube; Satoru Fujitus, Yamaguchi; Katsuro Masunaga; Hiroshi Yanagisawa, both of Ube, all of Japan

[73] Assignee: Ube Industries, Ltd., Yamaguchi, Japan

[21] Appl. No.: 338,242

[22] Filed: Jan. 11, 1982

[30] Foreign Application Priority Data

Jan. 23, 1981 [JP] Japan .................................. 56-7909
Jan. 23, 1981 [JP] Japan .................................. 56-7911
Jan. 26, 1981 [JP] Japan .................................. 56-9034

[51] Int. Cl.$^3$ .............................................. C07C 67/36
[52] U.S. Cl. .................................... 560/204; 502/327
[58] Field of Search ............ 560/204; 252/430, 431 C, 252/466 R, 466 PT

[56] References Cited

U.S. PATENT DOCUMENTS 4,138,587 2/1979 Yamasaki et al. ................... 560/204
4,229,589 10/1980 Nishimura et al. ................. 560/204
4,229,591 10/1980 Nishimura et al. ................. 560/204

*Primary Examiner*—Natalie Trousof
*Assistant Examiner*—Vera C. Clarke
*Attorney, Agent, or Firm*—Sherman & Shalloway

[57] ABSTRACT

In a process for preparing a diester of oxalic acid by the vapor phase catalytic reaction of carbon monoxide with an ester of nitrous acid in the presence of a catalyst composed of a solid carrier and a platinum-group metal or a salt thereof supported on the carrier, the improvement wherein said solid carrier is alumina having a specific surface area of not more than 90 m$^2$/g.

8 Claims, No Drawings

PROCESS FOR PREPARING OXALIC ACID DIESTERS USING PLATINUM GROUP METALS SUPPORTED ON ALUMINA

This invention relates to an improved process for preparing a diester of oxalic acid by the vapor (or gaseous) phase catalytic reaction of carbon monoxide with an ester of nitrous acid in the presence of a catalyst composed of a solid carrier and a platinum-group metal or a salt thereof supported on the carrier. According to this process, the diester of oxalic acid can be produced at a high space time yield (based on the platinum-group metal) and high selectivity with reduced formation of a carbonic acid diester and carbon dioxide as by-products. A further advantage of this process is that the amount of the platinum-group metal used can be decreased and it can be easily recovered.

More specifically, the present invention relates, in a process for preparing a diester of oxalic acid by the vapor phase catalytic reaction of carbon monoxide with an ester of nitrous acid in the presence of a catalyst composed of a solid carrier and a platinum-group metal or a salt thereof supported on the carrier, to the improvement wherein said solid carrier is alumina having a specific surface area of not more than 90 $m^2/g$.

The process for preparing a diester of oxalic acid by the vapor phase catalytic reaction of carbon monoxide with an ester of nitrous acid in the presence of a catalyst composed of a solid carrier and metallic palladium or a salt thereof supported on the carrier is known (U.S. Pat. No. 4,229,591). This patent cites active carbon, alumina, silica, diatomaceous earth, pumice, zeolite and molecular sieves as examples of the solid carrier. The patent, however, fails to disclose anything about the specific surface areas of alumina and other carriers and the choice of specific surface areas within a certain specified range.

In Example 14 of this U.S. patent in which the highest space time yield per unit weight of the platinum-group metal was achieved, the calculated space time yield is 581 mmol/g.Pd.hr and the calculated (assumed) selectivity of the diester of oxalic acid is 81.72%. In Example 1 in which the highest selectivity was achieved, the selectivity (assumed) of the diester of oxalic acid is 97.11%, and the space time yield is 89.9 mmol/g.Pd.hr.

Japanese Laid-Open Patent Publication No. 22666/1980 (published on Feb. 18, 1980; corresponding to UK patent application No. 2025950A) discloses another process for the production of a diester of oxalic acid by a similar vapor phase catalytic reaction to that shown in the above U.S. patent. The Japanese patent document exemplifies palladium, rhodium, iridium, platinum, gold and salts of these metals as ingredients of the catalyst, and silica, magnesium oxide, aluminum oxide, zinc oxide, $Cr_2O_3$ and pumice as examples of the carrier. It also exemplifies iron, copper, and salts of these as a carrier which concurrently serves as a catalyst promoter. However, it is quite silent on selectivity, and gives no data from which the selectivities of the reaction products can be calculated. In Example 10 of this patent publication in which the highest calculable space time yield was achieved, the space time yield was only 16.9 mmol/g.Rh.hr. Moreover, the Japanese Publication fails to disclose anything about the specific surface areas of alumina and other carriers and the choice of specific surface areas within a certain specified range.

Thus, it has been difficult in the art to achieve satisfactory results both in space time yield and selectivity, and an attempt to improve one of them has always resulted in reducing the other.

The present inventors have made investigations in order to provide an improved process for producing diesters of oxalic acid at a high space time yield (per unit weight of the platinum-group metal) and high selectivity. These investigations have led to the discovery that the specific surface area of an alumina carrier, which has been totally disregarded in the past, becomes an important factor which dominates the properties of a catalyst supported on the carrier. Specifically, the investigations of the present inventors have shown that a catalyst composed of an alumina carrier having a low specific surface area, particularly a specific surface area of not more than 90 $m^2/g$, preferably 0.05 to 70 $m^2/g$ and a platinum-group metal or a salt thereof supported on the carrier is useful for the production of diesters of oxalic acid at greatly improved space time yields (per unit weight of the platinum-group metal) and selectivities. It has also been found that the use of this catalyst supported on the low surface area carrier makes it possible to reduce the formation of a carbonic acid diester and carbon dioxide as by-products, to decrease the amount of the required platinum-group metal, and to recover the platinum-group metal easily.

It has further been found that an especially preferred catalyst composed of an alumina carrier having a specific surface area of not more than 90 $m^2/g$ and a platinum-group metal or a salt thereof supported on the carrier is obtained by impregnating the alumina carrier having a specific surface area of not more than 90 $m^2/g$ with an aqueous solution of a water-soluble salt of the platinum-group metal, treating the impregnated carrier with an alkali, and then subjecting the product to reducing treatment in the liquid or gaseous phase.

It is an object of this invention to provide an improved process for producing diesters of oxalic acid by vapor phase catalytic reaction.

The above and other objects and advantages of this invention will become more apparent from the following description.

The specific surface area ($m^2/g$), as used herein, denotes a specific surface area measured by the B.E.T. method utilizing the adsorption of nitrogen gas.

The catalyst used in the process of this invention is composed of an alumina carrier having a specific surface area of not more than 90 $m^2/g$ and a platinum-group metal or a salt thereof supported on the carrier.

Examples of the platinum-group metal are palladium, platinum, rhodium, ruthenium and iridium. These metals may, if desired, be used as a mixture of two or more. The use of palladium, either along or with another metal of the platinum group, is preferred. The salt of the platinum-group metal include nitrates, sulfates, phosphates, halides, acetates, oxalates, and benzoates of the above exemplified metals.

The alumina carrier has a specific surface area of not more than 90 $m^2/g$, for example 0.05 to 90 $m^2/g$, preferably 0.05 to 70 $m^2/g$. If the specific surface area of the alumina carrier becomes too high beyond the specified limit, the rate of the reaction between carbon monoxide and the nitrite becomes slow, and the space time yield, per unit weight of the platinum-group metal, of the oxalate decreases markedly with increasing amounts of by-products such as a carbonic acid diester. If the specific surface area of alumina is too low, it is difficult to support the platinum-group metal on it. For this reason, the preferred lower limit of the specific surface area is about 0.05 m²/g.

The alumina used in this invention needs not to be chemically pure, and may include a small amount, for example up to about 20% by weight, preferably up to about 15% by weight, of impurities. Such impurities include, for example, silica, carbon, silicon carbide, iron oxide, calcium oxide, sodium oxide and potassium oxide.

The amount of the catalytic metal component to be supported can be properly selected. It is preferably 0.01 to 10% by weight, more preferably 0.1 to 2% by weight, calculated as the metal based on the weight of the alumina carrier.

There is no restriction on the manner of supporting the catalytic metal component on the alumina carrier, and any known means of supporting can be used. Preferably, however, the catalyst is prepared by impregnating alumina having a specific surface area of not more than 90 m²/g with an aqueous solution of a water-soluble salt of the platinum-group metal, treating the impregnated alumina carrier with an alkali, and then subjecting the product to reducing treatment in the liquid or gaseous phase.

Examples of the water-soluble salt are nitrates, sulfates, acetates, phosphates, chlorides and sodium complex salts of the above-exemplified platinum-group metals.

The impregnation may be performed by dipping alumina in the aqueous solution of the platinum-group metal salt as a temperature of, for example, about 0° to about 90° C. for a period of, for example, about 0.1 to about 10 hours. If desired, it can be effected by spraying the aqueous solution of the platinum-group metal salt onto alumina. Preferably, the aqueous solution of the platinum-group metal salt is a solution prepared by dissolving the platinum-group metal salt in an acidic aqueous solution containing about 0.01 to about 10% by weight of an acidic compound. The use of the acidic aqueous solution serves to aid in the dissolving of the platinum-group metal and to prevent the formation and precipitation of a hydroxide and oxide of the platinum-group metal by hydrolysis.

Compounds having the anionic group of the platinum-group metal salt can generally be used as such acidic compounds. Specific examples include mineral acids such as hydrochloric acid, nitric acid, sulfuric acid and phosphoric acid and organic acids such as acetic acid. These acidic compounds may, if desired, be used as a mixture of two or more.

The alumina impregnated with the aqueous solution of the platinum-group metal salt is then separated, and if desired washed with water and then dried by, for example, air drying, vacuum drying or heat drying, after which it is subjected to the alkali treatment.

The alkali treatment can be effected by adding the alumina impregnated with the aqueous solution of the platinum-group metal salt to an alkaline aqueous solution containing about 0.5 to about 10% by weight of an alkaline compound, and stirring the mixture at a temperature of, for example, about 10° to about 90° C. for a period of, for example, about 0.5 to about 10 hours. Examples of the alkaline compound include the hydroxides and salts of alkali metals or alkaline earth metals, for example sodium hydroxide, potassium hydroxide, calcium hydroxide, barium hydroxide, sodium carbonate, sodium hydrogen carbonate and potassium carbonate. If desired, these alkaline compounds may be used as a mixture of two or more. There is no special limitation on the amount of the alkaline compound used. Preferably, it is about 2 to about 40 moles per mole of the platinum-group metal salt.

After the alkali treatment, the product is optionally washed with water, etc. and dried. The product is then treated with a reducing agent in the liquid or gaseous phase to form the final catalyst.

The liquid-phase reduction is carried out by using such reducing agents as hydrazine, formaldehyde, sodium formate and formic acid. Specifically, it can be carried out by adding the alkali-treated product to an aqueous solution of the reducing agent in a concentration of about 0.5 to about 10% by weight, and stirring the mixture at a temperature of, say, about 10° to about 50° C. for a period of, say, about 0.5 to about 10 hours.

The alkaline-treated product may be added directly to the aqueous solution of the reducing agent in performing the reduction. It is more effective, however, to separate the alkali-treated solid product by a solid-liquid separating procedure such as filtration or decantation, wash and dry it in the manner described above, and then add the dried product to the aqueous solution of the reducing agent in the liquid phase.

Examples of reducing agents suitable for use in the gaseous phase reduction are hydrogen, carbon monoxide and ammonia. These reducing agents may be used after being diluted with inert gaseous such as nitrogen or carbon dioxide. The gaseous phase reduction can be carried out by passing the gaseous reducing agent through the alkali-treated product at a temperature of, for example, about 100° to about 500° C. for a period of, say, about 0.5 to about 10 hours.

The starting gases used in the synthesis of diesters of oxalic acid in accordance with the process of this invention are carbon monoxide and a nitrous acid ester, and as required, may also include an alcohol, a nitrogen oxide, etc. to be described hereinbelow. In any case, the starting gases include carbon monoxide which is effective for the aforesaid reducing treatment. Thus, the gaseous phase reduction of the alkali-treated product may also be effected by a procedure which comprises filling the alkali-treated product into a reactor for the synthesis of a diester of oxalic acid, and prior to the synthesis of the diester of oxalic acid, treating it with a starting gaseous mixture of carbon monoxide and a nitrous acid ester optionally containing an alcohol, a nitrogen oxide, etc.

The final desired catalyst can be formed by performing the reduction in the above manner. In the case of the liquid phase reduction, the treated product may be washed with water, etc. and dried.

According to the process of this invention, carbon monoxide is reacted with an ester of nitrous acid in the vapor phase in the presence of the resulting catalyst composed of alumina having a specific surface area of not more than 90 m²/g and a platinum-group metal or a salt thereof supported on the carrier. This reaction can schematically be shown below.

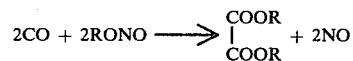

(R = alkyl or cycloalkyl)

As the above scheme shows, this reaction yields nitrogen monoxide equivalent to the consumed nitrous acid ester. Accordingly, the nitrogen monoxide thus formed may be recycled as the starting material for the above reaction by introducing an alcohol and a gas containing molecular oxygen to react them with the nitrogen monoxide as schematically shown below and recovering the resulting nitrous acid ester.

$$2NO + \tfrac{1}{2}O_2 + 2ROH \rightarrow 2RONO + H_2O$$

(R = alkyl or cycloalkyl)

An ester of nitrous acid with a saturated monohydric aliphatic alcohol having 1 to 8 carbon atoms or an alicyclic alcohol having 1 to 8 carbon atoms is preferred as the ester of nitrous acid. Examples of the aliphatic alcohol are methanol, ethanol, n-propanol, isopropanol, n-butanol, isobutanol, sec-butanol, tert-butanol, n-amyl alcohol, isoamyl alcohol, hexanol and octanol, and examples of the alicyclic alcohol include cyclohexanol, and methylcyclohexanol. These alcohols may contain a substituent, such as an alkoxy group, which does not inhibit the reaction.

The concentration of the ester of nitrous acid used may be varied over a wide range. To obtain a satisfactory rate of reaction, it is desirable to adjust the concentration of the nitrous acid ester in the starting gaseous mixture introduced into the reactor at 1% by volume or higher, for example about 5 to about 30% by volume.

Carbon monoxide used in the process of this invention may be pure or may be diluted with an inert gas such as nitrogen. The concentration of carbon monoxide in the reaction zone may be varied over a wide range and is usually in the range of 10 to 90% by volume.

The reaction is carried out under such conditions that no liquid phase is formed in the reaction zone (namely, in the gaseous or vapor phase). These conditions may vary depending upon the reaction temperature, the reaction pressure, the type and concentration of the nitrous acid ester, etc. Thus, these conditions may be properly selected so that the reaction is carried out in the vapor phase.

The reaction proceeds rapidly even at low temperatures, and side-reactions occurs less as the reaction temperature is lower. Hence, it is desirable to perform the reaction at relatively low temperature at which the desired space time yield can be maintained, for example at a temperature of about 50° C. to about 200° C., preferably at about 80° C. to about 150° C. The reaction pressure can also be selected properly. For example, it is atmospheric pressure to about 10 kg/cm$^2$.G, preferably atmospheric pressure to about 5 kg/cm$^2$.G. Pressures below the abovespecified lower limit, for example reduced pressures of down to about 200 mmHg, can also be used.

The catalytic reaction in accordance with this invention may be carried out in a fixed or fluidized bed. The time of contact between the starting gaseous mixture and the catalyst can be properly chosen. For example, the contact time is not more than about 20 seconds, preferably about 0.2 to about 10 seconds.

The nitrous acid ester can be prepared, for example, by reacting an alcohol with a nitrogen oxide in the optional presence of molecular oxygen. The reaction product gas contains the unreacted alcohol and nitrogen oxide (particularly nitrogen monoxide) and at times, traces of water and oxygen in addition to the desired nitrous acid ester. In the process of this invention, this product gas containing the nitrous acid ester can be used as the starting nitrous acid ester, and the platinum-group metal catalyst supported on alumina having a specific surface area of not more than 90 m$^2$/g exhibits very high catalytic activity even when a nitrous acid ester containing such impurities is used.

The following examples illustrate the present invention more specifically.

CATALYST PREPARATION EXAMPLE 1

Palladium chloride (0.77 part by weight) was dissolved in 34.2 parts by weight of a 0.93% by weight aqueous solution of hydrochloric acid, and 30 parts by weight of alumina having a specific surface area of about 3.1 m$^2$/g was dipped in the solution. The solution was stirred at room temperature for about 2 hours.

The alumina impregnated with palladium chloride was separated by decantation, dried, and then dipped in a solution consisting of 0.5 part by weight of sodium hydroxide, 0.7 part by weight of sodium hydrogen carbonate and 48.8 parts by weight of water. The solution was stirred at about 70° C. for about 9 hours to perform alkali treatment.

The alkali-treated product was washed with water until the washing became neutral and a chlorine ion was no longer detected. The product was then dipped in an aqueous hydrazine solution consisting of 3 parts by weight of 85% hydrazine hydrate and 97 parts by weight of water, and the solution was stirred at room temperature for about 4 hours to perform the reducing treatment.

The reduction product was decanted, washed with water and dried to give a spherical supported catalyst having a particle diameter of 3 mm and composed of alumina and 0.44% of palladium supported on it.

EXAMPLE 1

Ten milliliters (9.8 g) of the supported catalyst prepared in Catalyst Preparation Example 1 was filled in a glass reaction tube having an inside diameter of 20 mm and a length of 55 cm. Furthermore, glass beads were filled into the reaction tube and thus placed on the catalyst layer to a height of 20 cm.

The reaction tube was fixed vertically, and an annular electric heater was mounted on the outside of the reactor to heat the catalyst layer at 110° C.

From the top of the reaction tube, carbon monoxide, gaseous methyl nitrite, nitrogen monoxide, gaseous methanol and nitrogen were fed into the reactor at a rate of 4, 3, 0.6, 3, and 9.4 Nl/hr, respectively, and reacted at atmospheric pressure.

The reaction mixture which left the reaction tube was passed through methanol to collect dimethyl oxalate. Low-boiling compounds which were not collected by methanol were then condensed by cooling with dry ice/methanol and collected. The collected liquids were respectively analyzed by gas chromatography. The results are shown in Table 1.

EXAMPLES 2 TO 6 AND COMPARATIVE EXAMPLES 1

Spherical alumina-supported palladium catalysts having a particle diameter of 3 mm were prepared in the same way as in Catalyst Preparation Example 1 except that alumina having various specific surface areas shown in Table 1 was used. using 10 ml of each of the catalysts, dimethyl oxalate was synthesized by the same procedure as in Example 1. The results are shown in Table 1.

COMPARATIVE EXAMPLES 2 AND 3

A cylindrical silica-alumina-supported palladium catalyst having a particle diameter of 1 mm and a particle height of 4 to 5 mm was prepared in the same way as in Catalyst Preparation Example 1 except that silica (71%)-alumina (28%) was used instead of alumina (Comparative Example 2).

A cylindrical zeolite-supported palladium catalyst having a particle diameter of 2 mm and a particle height of 2 to 3 mm was prepared in the same way as in Catalyst Preparation Example 1 except that zeolite was used instead of alumina (Comparative Example 3).

Using 10 ml of each of the catalysts, dimethyl oxalate was synthesized by the same procedure as in Example 1. The results are also shown in Table 1.

The results given in Table 1 demonstrate that the oxalate can be obtained in a high yield and selectivity in the present invention, but when other known carriers and alumina carriers outside the scope of the invention were used, the space time yield per gram of Pd and selectivity of the dioxalate are very low.

tivities of these products based on carbon monoxide were 97.8, 1.9 and 0.4%, respectively.

EXAMPLE 8

Ten milliliters (8.7 g) of a spherical palladium catalyst having a particle diameter of 3 mm and containing 0.5% by weight of palladium supported on alumina having a specific surface area of 8.7 m$^2$/g, which was prepared in a manner similar to that in Catalyst Preparation Example 1, was filled in a glass reaction tube having an inside diameter of 20 mm and a length of 55 cm. Glass beads were further filled in the reaction tube and placed on the catalyst layer to a thickness of 20 cm.

The reaction tube was fixed vertically, and an annular electric heater was mounted on the outside of the reaction tube to heat the catalyst layer at 110° C.

From the top of the reaction tube, a gaseous mixture consisting of 20% by volume of carbon monoxide, 15% by volume of methyl nitrite and 65% by volume of nitrogen was fed into the reactor at a rate of 20 Nl/hr, and reacted at atmospheric pressure.

The reaction mixture was worked up in the same way as in Example 1.

The amounts of dimethyl oxalate, dimethyl carbonate and carbon dioxide gas formed were 43.10, 1.58, and

TABLE 1

| | | Catalyst | | | | | |
| | | Specific surface area of carrier (m$^2$/g) | Amount of palladium supported (wt. %) | Amount used (g) | Amounts of products formed (mmol/hr) (*) | | | Space time yield of dimethyl oxalate based on palladium (mmol/g.Pd.hr) |
| | carrier | | | | Dimethyl oxalate | Dimethyl carbonate | Carbon dioxide | |
|---|---|---|---|---|---|---|---|---|
| Example | | | | | | | | |
| 1 | Alumina | 3.1 | 0.44 | 9.8 | 41.43 (97.2%) | 2.04 (2.4%) | 0.36 (0.4%) | 961 |
| 2 | Alumina | 1.0 | 0.67 | 10.5 | 38.14 (98.2%) | 1.11 (1.4%) | 0.27 (0.4%) | 542 |
| 3 | Alumina | 6.3 | 0.67 | 8.7 | 41.81 (97.8%) | 1.80 (2.1%) | 0.50 (0.6%) | 718 |
| 4 | Alumina | 15 | 0.50 | 10.4 | 38.98 (96.6%) | 2.04 (2.5%) | 0.76 (0.9%) | 750 |
| 5 | Alumina | 48 | 0.50 | 8.8 | 37.95 (95.7%) | 2.70 (3.4%) | 0.71 (0.9%) | 863 |
| 6 | Alumina | 62 | 0.50 | 8.3 | 35.64 (94.8%) | 2.95 (3.9%) | 0.97 (1.3%) | 860 |
| Comparative Example | | | | | | | | |
| 1 | Alumina | 97 | 0.43 | 9.3 | 9.62 (93.0%) | 0.76 (3.7%) | 0.69 (3.3%) | 242 |
| 2 | Silica-Alumina | 0.1 | 242 | 3.4 | 9.45 (91.6%) | 1.19 (5.8%) | 0.54 (2.6%) | 279 |
| 3 | Zeolite | 382 | 1.0 | 5.8 | 4.92 (94.3%) | 0.33 (3.2%) | 0.27 (2.5%) | 85 |

(*) The parenthesized figures are selectivities based on carbon monoxide.

EXAMPLE 7

A spherical supported catalyst having a particle diameter of 3 mm and composed of alumina and 0.41% of palladium supported on it was prepared in the same way as in Catalyst Preparation Example 1 except that alumina having a purity of 85.5% (the main component of the remainder was 13% silica) and a specific surface area of 1 m$^2$/g was used instead of the alumina used in Catalyst Preparation Example 1. By using 10 ml (11.2 g) of the resulting catalyst, dimethyl oxalate was synthesized by the same procedure as in Example 1 except that the reaction temperature was changed to 120° C.

The amounts of dimethyl oxalate, dimethyl carbonate and carbon dioxide formed were 32.42 mmol/hr (the space time yield based on Pd=707 mmol/g.Pd.hr), 1.25 mmol/hr, and 0.23 mmol/hr, respectively. The selec- 0.40 mmol/hr, respectively, and the selectivities of these products based on carbon monoxide were 97.8, 1.8, and 0.5%, respectively. The space time yield of dimethyl oxalate based on Pd was 992 mmol/g.Pd.hr.

EXAMPLE 9

The procedure of Example 1 was followed except that 10 ml (8.7 g) of a spherical palladium catalyst having a particle diameter of 3 mm and composed of alumina having a specific surface area of 6.3 m$^2$/g and 0.44% by weight of palladium supported on it, which was prepared in the same way as in Catalyst Preparation Example 1, was used, and carbon monoxide, gaseous ethyl nitrite, nitrogen monoxide, gaseous ethanol and nitrogen were fed into the reaction tube from its top at a rate of 4, 1.2, 0.6, 3 and 11.2 Nl/hr, respectively.

Diethyl oxalate was formed in an amount of 18.67 mmole/hr (space time yield based on Pd=490 mmol/g.Pd.hr). As by-products only 0.47 mmole/hr of diethyl carbonate and 0.53 mmol/hr of carbon dioxide gas were formed. The selectively of diethyl oxalate based on Co was 94.6%.

EXAMPLE 10

Ten milliliters (8.7 g) of a spherical palladium catalyst having a particle diameter of 3 mm and composed of alumina having a specific surface area of 8.7 m$^2$/g and 0.5% by weight of palladium supported on it, which was prepared in accordance with the method set forth in Catalyst Preparation Example 1, was filled in a stainless steel reaction tube having an inside diameter of 23 mm and a length of 55 cm. Glass beads were filled into the reaction tube and placed on the catalyst layer to a height of 20 cm. The reaction tube was fixed vertically, and an annular electric heater was mounted on the outside of the reaction tube to heat the catalyst layer at 110° C.

From the top of the reaction tube, a gaseous mixture consisting of 20% by volume of carbon monoxide, 15% by volume of methyl nitrite, 3% by volume of nitrogen monoxide, 4% by volume of methanol and 58% by volume of nitrogen was fed into the reaction tube at a rate of 18.6 Nl/hr, and reacted at a pressure of 2.0 kg/cm$^2$.G.

The reaction product which left the reaction tube was passed through methanol to collect dimethyl oxalate. Low-boiling compounds not collected by methanol were then condensed by cooling with dry ice/methanol and collected. The liquids collected were each analyzed by gas chromatography.

It was found that dimethyl oxalate was obtained in a space time yield of 666 mmol/g.Pd.hr, and based on carbon monoxide, the selectivities of dimethyl oxalate, dimethyl carbonate and carbon dioxide gas were 95.5, 2.0, and 0.7%, respectively.

EXAMPLE 11

The procedure of Example 10 was followed except that a gaseous mixture consisting of 20% by colume of carbon monoxide, 9.2% by volume of methyl nitrite, 3% by volume of nitrogen monoxide, 2% by volume of methanol and 65.8% by volume of nitrogen was fed into the reactor from its top, and reacted under a pressure of 4.6 kg/cm$^2$.G.

Dimethyl oxalate was obtained in a space time yield of 654 mmole/g.Pd.hr. The selectivities of dimethyl oxalate, dimethyl carbonate and carbon dioxide gas based on carbon monoxide were 95.8, 2.4, and 2.1%, respectively.

CATALYST PREPARATION EXAMPLE 2

Palladium chloride (9.43 parts by weight) was dissolved in 410 parts by weight of a 0.93% aqueous solution of hydrochloric acid, and 400 parts by weight of alumina having a specific surface area of 7 m$^2$/g was dipped in the solution. The solution was stirred at room temperature for about 2 hours. The alumina impregnated with palladium chloride was separated by decantation, dried in the air and then dried at 120° C. overnight.

120 parts by weight of the dried product was dipped in 200 parts by weight of an aqueous solution containing 1% by weight of sodium hydroxide and 1.4% by weight of sodium hydrogen carbonate. The solution was stirred at about 70° C. for 4 hours to perform alkali treatment.

The alkali-treated product was then washed with warm water until the washing became neutral and a chlorine ion was no longer detected. It was then dried overnight at 80° C.

The alkali-treated product was dipped in a 3 wt. % aqueous solution of hydrazine. The solution was stirred at room temperature for 4 hours to perform reducing treatment. The treated product was then washed with water and dried to give a catalyst composed of alumina and 0.56% by weight of palladium supported on it.

EXAMPLE 12

The procedure of Example 1 was followed except that the catalyst obtained in Catalyst Preparation Example 2 was used in an amount of 10 ml (8.7 g) instead of the catalyst used in Example 1. The results are shown in Table 3.

EXAMPLES 13 TO 21

Catalysts were prepared in the same way as in Catalyst Preparation Example 2 by changing the alkali-treating agent, the treating temperature and the reducing agent as shown in Table 3. Using 10 ml (8.7 g) of these catalysts, dimethyl oxalate was prepared in the same way as in Example 1. The results are also shown in Table 2.

TABLE 2

| | Catalyst | | | Amounts of products formed (mmol/hr) (*) | | | Space time yield of dimethyl oxalate based on Pd (mmol/g.Pd/hr) |
|---|---|---|---|---|---|---|---|
| Example | Alkali treatment | Reducing treatment | Amount of Pd supported (wt. %) | Dimethyl oxalate | Dimethyl carbonate | Carbon dioxide | |
| 12 | 1 wt % NaOH 1.4 wt % NaHCO$_3$ 70° C. | Hydrazine | 0.56 | 38.92 (97.88%) | 1.27 (1.60%) | 0.42 (0.53%) | 800 |
| 13 | 1.6 wt % NaOH 70° C. | Hydrazine | 0.55 | 40.12 (97.93%) | 1.31 (1.60%) | 0.39 (0.48%) | 838 |
| 14 | wt % NaOH 50° C. | Hydrazine | 0.57 | 40.74 (98.10%) | 1.21 (1.46%) | 0.37 (0.44%) | 822 |
| 15 | wt % NaOH 25° C. | Hydrazine | 0.49 | 41.64 (97.64%) | 1.59 (1.88%) | 0.40 (0.47%) | 968 |
| 16 | 2.6 wt % NaOH 50° C. | Hydrazine | 0.58 | 36.89 (97.42%) | 1.26 (1.67%) | 0.69 (0.91%) | 731 |
| 17 | 0.8 wt % NaOH 50° C. | Hydrazine | 0.56 | 40.09 (97.47%) | 1.18 (1.43%) | 0.90 (1.09%) | 823 |
| 18 | 0.4 wt % NaOH 50° C. | Hydrazine | 0.56 | 37.75 (96.95%) | 1.43 (1.84%) | 0.94 (1.21%) | 776 |
| 19 | 2.2 wt % KOH | Hydrazine | 0.49 | 32.63 | 0.67 | 0.21 | 773 |

TABLE 2-continued

| | Catalyst | | | Amounts of products formed (mmol/hr) (*) | | | Space time yield of dimethyl oxalate based on Pd (mmol/g.Pd/hr) |
|---|---|---|---|---|---|---|---|
| Example | Alkali treatment | Reducing treatment | Amount of Pd supported (wt. %) | Dimethyl oxalate | Dimethyl carbonate | Carbon dioxide | |
| 20 | 3.3 wt % Ba(OH)$_2$ 70° C. | Hydrazine 70° C. | 0.36 | 32.83 (98.67%) | 0.92 (1.01%) | 0.24 (0.32%) | 1047 |
| 21 | 1 wt % NaOH 1.4 wt % NaHCO$_3$ 70° C. | Sodium formate | 0.52 | 37.17 (98.26%) (98.15%) | 1.05 (1.38%) (1.39%) | 0.35 (0.36%) (0.46%) | 822 |

(*) The parenthesized figures are selectivities based on carbon monoxide.

CATALYST PREPARATION EXAMPLE 3

Palladium chloride (9.43 parts by weight) was dissolved in 410 parts by weight of a 0.93% by weight aqueous solution of hydrochloric acid, and 400 parts by weight of alumina having a specific surface area of 7 m$^2$/g and a particle diameter of 3 mm was dipped in the solution. The solution was stirred at room temperature for about 2 hours. The alumina impregnated with palladium chloride was separated by decantation, dried in the air, and then dried overnight at 120° c.

120 Parts by weight of the dried product was dipped in 200 parts by weight of an aqueous solution containing 1% by weight of sodium hydroxide and 1.4% by weight of sodium hydrogen carbonate. The solution was stirred at about 70° C. for 4 hours to perform alkali treatment.

The alkali-treated product was washed with warm water until the washing became neutral and a chlorine ion was no longer detected. The washed product was then dried overnight at 80° C.

The alkali-treated product was then subjected to reducing treatment at 300° C. for 5 hours in a stream of hydrogen to give a catalyst composed of alumina and 0.52% by weight of palladium supported on it.

EXAMPLE 22

The procedure of Example 1 was followed except that the catalyst prepared in Catalyst Preparation Example 3 was used instead of the catalyst used in Example 1. The results are shown in Table 3.

EXAMPLE 23

A catalyst was prepared in the same way as in Catalyst Preparation Example 3 except that the reducing agent was changed as shown in Table 3. The procedure of Example 1 was followed except that the catalyst was changed to the above catalysts. The results are shown in Table 3.

EXAMPLE 24

An alumina-supported palladium catalyst was obtained by the same procedure as in Catalyst Preparation Example 3 except that the reducing treatment of the alkali-treated product was carried out in a gaseous mixture consisting of 20% by volume of carbon monoxide, 15% by volume of methyl nitrite, 3% by volume of nitrogen monoxide and 15% by volume of methanol and 47% by volume of nitrogen at 110° C. for 1 hour. Using the resulting catalyst, dimethyl oxalate was prepared in the same way as in Example 1. The results are shown in Table 3.

TABLE 3

| | Catalyst | | | | Amounts of products formed (mmol/hr) (**) | | | Space time yield based on Pd of dimethyl oxalate |
|---|---|---|---|---|---|---|---|---|
| Example | Carrier | Alkali treatment | Reduction | Amount of Pd supported (wt. %) | Dimethyl oxalate | Dimethyl carbonate | Carbon dioxide | |
| 22 | Alumina | 70° C., 4 hrs. | H$_2$, 300° C. 5 hrs. | 0.52 | 38.64 (97.60%) | 1.51 (1.91%) | 0.39 (0.49%) | 854 |
| 23 | Alumina | 70° C., 4 hrs. | CO, 300° C., 5 hrs. | 0.52 | 34.34 (97.49%) | 1.41 (2.00%) | 0.36 (0.51%) | 759 |
| 24 | Alumina | 70° C., 4 hrs. | 20 vol. % CO, 110° C., 1 hr. | 0.51 | 38.79 (97.41%) | 1.45 (1.82%) | 0.62 (0.78%) | 875 |

(*) The amount of the catalyst used is 10 ml (8.7 g).
(**) The parenthesized figures are selectivities based on carbon monoxide.

EXAMPLE 25

The procedure of Example 1 was followed except that 2 ml (1.74 g) of a spherical palladium catalyst having a particle diameter of 3 mm and composed of alumina having a specific surface area of 6.3 m$^2$/g and 0.56% by weight of palladium supported on it, which was prepared in accordance with the method set forth in Catalyst Preparation Example 1, was used instead of the catalyst used in Example 1. The results are shown in Table 4 below.

TABLE 4

| Selectivity based on CO (%) | | | Space time yield | | |
|---|---|---|---|---|---|
| Dimethyl oxalate | Dimethyl carbonate | Carbon dioxide | g/l.hr | mmol/l.hr | mmol/g. Pd.Hr |
| 98.0 | 1.7 | 0.3 | 1,148 | 9,729 | 1,997 |

What we claim is:

1. In a process for preparing a diester of oxalic acid by the vapor phase catalytic reaction of carbon monoxide with an ester of nitrous acid in the presence of a catalyst composed of a solid carrier and a platinum-group metal or a salt thereof supported on the carrier, the improvement wherein said solid carrier is alumina having a specific surface area of not more than 90 m²/g.

2. The process of claim 1 wherein the ester of nitrous acid is an ester of nitrous acid with an alcohol having 1 to 8 carbon atoms selected from the group consisting of saturated monohydric aliphatic alcohols and alicyclic alcohols.

3. The process of claim 1 wherein the alumina has a specific surface area of 0.05 to 70 m²/g.

4. The process of claim 1 wherein the reaction is carried out at a temperature of about 50° C. to about 200° C.

5. The process of claim 1 wherein the reaction is carried out at atmospheric pressure to about 10 kg/cm².G.

6. The process of claim 1 wherein the amount of the platinum-group metal supported is 0.01 to 10% by weight, as metal, based on the weight of the alumina carrier.

7. The process of claim 1 wherein the catalyst is prepared by impregnating the alumina having a specific surface area of not more than 90 m²/g with an aqueous solution of a water soluble salt of the platinum-group metal, treating the impregnated alumina with an alkali, and then subjecting the alkali-treated product to reduction in the liquid or gaseous phase.

8. The process of claim 7 wherein the alkali is a hydroxide, carbonate or bicarbonate of an alkali metal or an alkaline earth metal.

* * * * *